(12) United States Patent
Patterson

(10) Patent No.: US 11,338,456 B2
(45) Date of Patent: May 24, 2022

(54) TRIMSAFE HISTOLOGY RADIUS BLADE GROSSING KNIFE

(71) Applicant: Belair Instrument Company, LLC, Springfield, NJ (US)

(72) Inventor: Barry Patterson, Springfield, NJ (US)

(73) Assignee: BELAIR INSTRUMENT COMPANY, LLC, Springfield, NJ (US)

( * ) Notice: Subject to any disclaimer, the term of this patent is extended or adjusted under 35 U.S.C. 154(b) by 43 days.

(21) Appl. No.: 16/668,645

(22) Filed: Oct. 30, 2019

(65) Prior Publication Data

US 2020/0276723 A1 Sep. 3, 2020

Related U.S. Application Data

(60) Provisional application No. 62/811,918, filed on Feb. 28, 2019.

(51) Int. Cl.

| | | |
|---|---|---|
| *B26B 5/00* | (2006.01) | |
| *A01B 1/22* | (2006.01) | |
| *A61B 17/3213* | (2006.01) | |
| *B25G 3/12* | (2006.01) | |
| *A61B 17/3211* | (2006.01) | |

(52) U.S. Cl.
CPC ............... *B26B 5/00* (2013.01); *A01B 1/22* (2013.01); *A01B 1/227* (2013.01); *A61B 17/3211* (2013.01); *A61B 17/3213* (2013.01); *B25G 3/12* (2013.01)

(58) Field of Classification Search
CPC ............ A61B 17/3213; A61B 17/3211; A61B 17/32113; B26B 5/00; B26B 5/007; B21D 53/64; A01B 1/227; A01B 1/22; A22C 25/006; B25G 3/00; B25G 3/02; B25G 3/08; B25G 3/12; B25G 3/14; B25G 3/18; B25G 3/26

See application file for complete search history.

(56) References Cited

U.S. PATENT DOCUMENTS

| | | | | |
|---|---|---|---|---|
| 1,090,398 | A | * | 3/1914 | Humeston ................. B26B 5/00 30/329 |
| 1,625,778 | A | * | 4/1927 | Nickerson .......... A61B 17/3213 279/37 |
| 1,706,251 | A | * | 3/1929 | Perry ........................ B26B 5/00 30/337 |

(Continued)

FOREIGN PATENT DOCUMENTS

WO WO-2015173823 A1 * 11/2015 ............... B26B 5/00

*Primary Examiner* — Evan H Macfarlane
(74) *Attorney, Agent, or Firm* — Dunlap Bennett & Ludwig, PLLC

(57) ABSTRACT

A histology radius blade grossing knife is provided. The histology radius blade grossing knife has a blade mounting system adapted to operatively retain a histology radius trimming blade. The blade mounting system provides a retaining spine for engaging an upper edge of the trimming blade, wherein a rear portion of the retaining spine is securely sandwiched by retaining plates of the blade mounting system. Furthermore, the trimming blade provides notches and/or recesses for facilitating such operative association. Each histology radius trimming blade embodies a radiused or otherwise uniquely shaped heel for cutting and dissecting tissue.

5 Claims, 5 Drawing Sheets

(56) References Cited

U.S. PATENT DOCUMENTS

| | | | | |
|---|---|---|---|---|
| 1,813,498 A | * | 7/1931 | Kosunen | B26B 5/00 |
| | | | | 30/317 |
| 1,813,723 A | * | 7/1931 | Beaver | B26B 5/00 |
| | | | | 279/77 |
| 1,940,855 A | * | 12/1933 | Friedman | A61B 17/3213 |
| | | | | 279/24 |
| 1,998,188 A | * | 4/1935 | Dunn | B26B 5/00 |
| | | | | 279/77 |
| 2,134,973 A | * | 11/1938 | Harwell | B26B 5/006 |
| | | | | 30/156 |
| 2,439,071 A | * | 4/1948 | Basham | B25G 3/18 |
| | | | | 279/77 |
| D743,236 S | * | 11/2015 | Fischer | D8/99 |
| 2005/0252010 A1 | * | 11/2005 | Freeman | B26B 5/00 |
| | | | | 30/336 |
| 2014/0345147 A1 | * | 11/2014 | Frazer | B26B 11/006 |
| | | | | 30/336 |
| 2017/0151682 A1 | * | 6/2017 | Cheng | B26B 5/00 |
| 2017/0348863 A1 | * | 12/2017 | Kommer | B26B 9/00 |

* cited by examiner

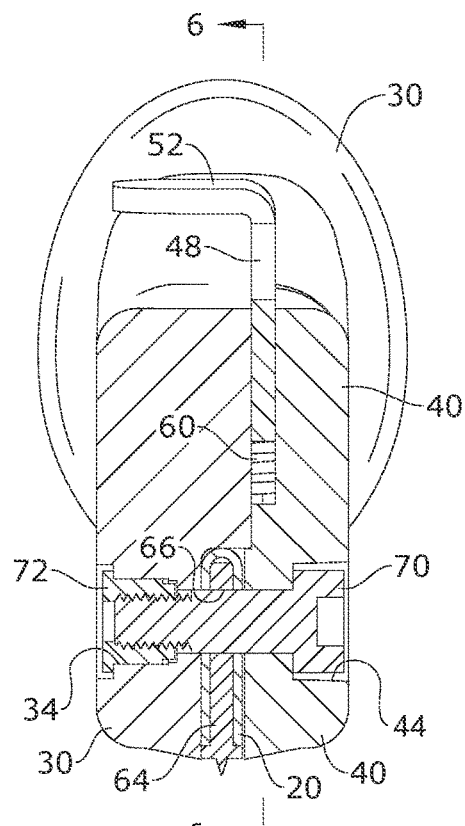
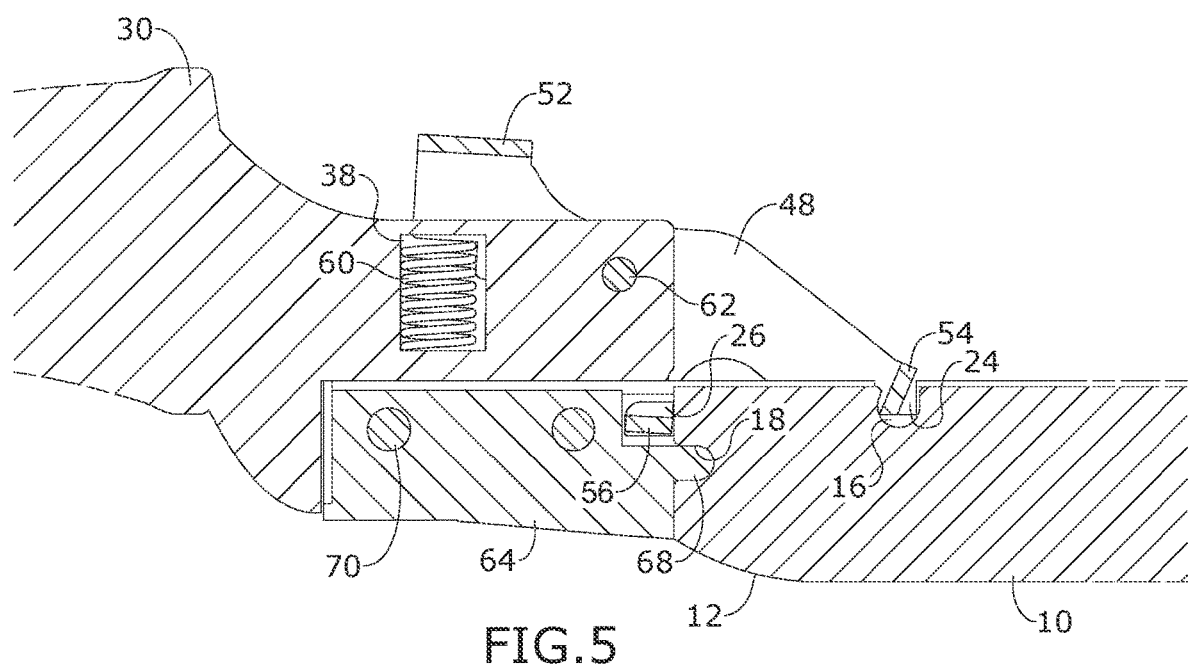

TRIMSAFE HISTOLOGY RADIUS BLADE GROSSING KNIFE

CROSS-REFERENCE TO RELATED APPLICATION

This application claims the benefit of priority of U.S. provisional application No. 62/811,918, filed 28 Feb. 2019, the contents of which are herein incorporated by reference.

BACKGROUND OF THE INVENTION

The present invention relates to trimming knife blades and, more particularly, a histology radius blade grossing knife.

Current trimming blades have a square corner blade that can catch or drag through the specimen being cut. Moreover, current grossing knives have the trimming blade retained in the blade holder with a small thumb screw, which has a tendency to become loose, risking imprecise cuts and jeopardizing the safety of the user.

As can be seen, there is a need for a histology radius blade grossing knife having a blade mounting system adapted to operatively retain a histology radius trimming blade wherein the histology radius trimming blade embodies a radiused or otherwise uniquely shaped heel for cutting and dissecting tissue specimens. The trimming blades (colloquially known as the "TrimSafe Blade") embodied by the present invention have a radiused or otherwise uniquely shaped heel that is dimensioned and adapted to dramatically improve how the blade moves through the cut. Specifically, the TrimSafe Blade design includes trimming blades with a radiused, angled, segmented, faceted, or otherwise relieved or eased heel.

The histology radius blade grossing knife has a blade mounting system adapted to operatively associate with a plurality of interchangeable, replaceable, and disposable histology radius trimming blades. The blade mounting system provides a retaining spine for engaging the trimming blade, while the trimming blade provides notches and/or recesses for facilitating such operative association. Each histology radius trimming blade embodies a radiused or otherwise uniquely shaped heel for cutting and dissecting tissue specimens taken from patients in medical laboratories for anatomical pathology applications, including but not limited to grossing, sectioning, post-mortem examination, and medical research.

Moreover, the TrimSafe Blade grossing knife utilizes a thumb latch locking tab that seats into recesses or notches in the trimming blade that eliminates the securing screw approach of the prior art, thereby dramatically improving the safety, simplicity and ease of use for the user.

SUMMARY OF THE INVENTION

In one aspect of the present invention, a histology trimming blade for anatomical pathology applications includes the following: an elongated body defined by opposing lower and upper longitudinal portions, a front portion, and a rear portion; the cutting edge and the upper edge disposed along opposing lower and upper longitudinal portions, respectively; and the cutting edge having a relieved heel, wherein the relieved heel is defined by an absence of the elongated body for a run along the cutting edge of approximately 0.50 inches from the rear portion and a rise along the rear portion of approximately 0.16 inches from the cutting edge. Wherein certain embodiments the relieved heel is further defined by a curved cutting edge having a radius of approximately one inch, or is further defined a straight cutting edge defined by the rise and run, or is further defined a first and second segmented cutting edges defined by the rise and run, wherein the segmented cutting edges are oblique relative to each other and the second segmented cutting edge is longer than the first segmented cutting edge. The histology trimming blade for anatomical pathology applications may also include a lock notch in the upper portion, and a stop notch in the rear portion.

In another aspect of the present invention, a histology radius blade grossing knife for removably engaging the above-mentioned histology trimming blade includes the following: a handle; a spine for retaining the upper portion of said histology trimming blade; a blade mounting system connected to the handle; the blade mounting system provides a first and second retaining plates for sandwiching a proximal end of the spine; a thumb latch having a locking tab; and the thumb latch pivotably connected to the blade mounting system for pivoting between an open position and a locked position wherein the locking tab engages the lock notch, wherein the spine provides a distal portion and a proximal portion, wherein for the distal portion two lengthwise edges taper toward each other so as provide lateral support of the received said histology trimming blade; and further including a blade stop nested between the lengthwise edges of the proximal end; and the blade stop provides a protruding stop tab that mates with the stop notch, wherein the proximal portion provides a tab slot for engaging the thumb latch during pivoting.

These and other features, aspects and advantages of the present invention will become better understood with reference to the following drawings, description and claims.

BRIEF DESCRIPTION OF THE DRAWINGS

FIG. 4 is a section view of an exemplary embodiment of the present invention, taken along line 4-4 in FIG. 1;

FIG. 5 is a section view of an exemplary embodiment of the present invention, taken along line 5-5 in FIG. 2;

DETAILED DESCRIPTION OF THE INVENTION

Figure 1:
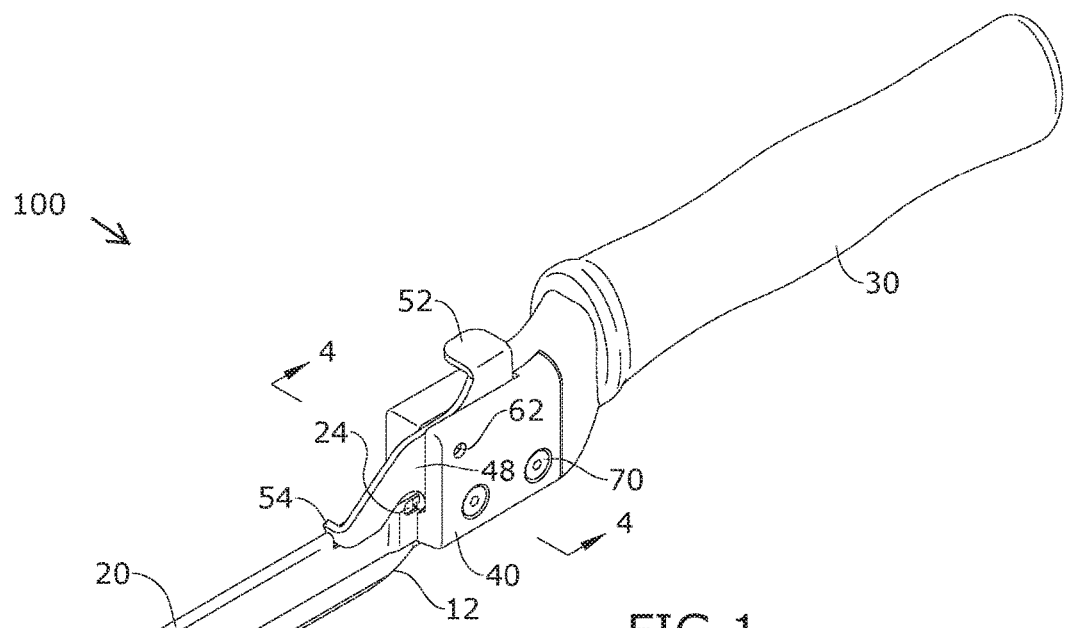
FIG. 1 is a front perspective view of an exemplary embodiment of the present invention.
Figure 2:
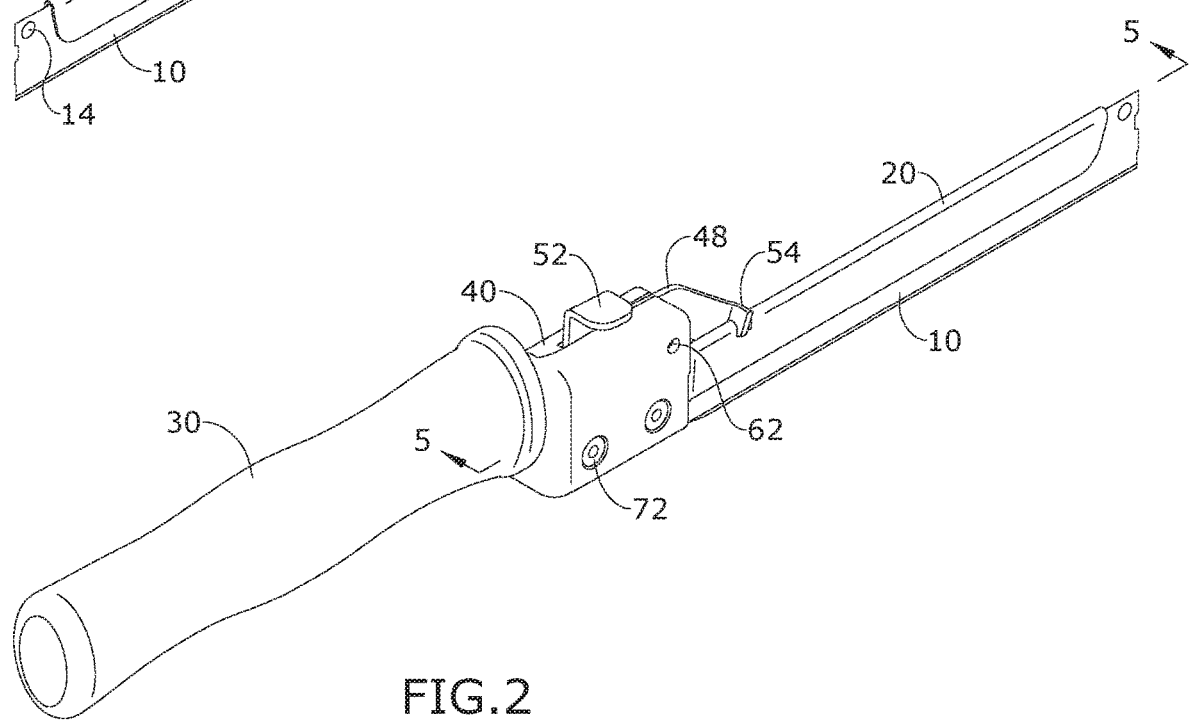
FIG. 2 is a rear perspective view of an exemplary embodiment of the present invention.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a histology radius blade grossing knife having a blade mounting system adapted to operatively retain a histology radius trimming blade. The blade mounting system provides a retaining spine for retaining an upper edge of the trimming blade, while the trimming blade provides notches and/or recesses for facilitating such operative association by way of a thumb latch and stop blade provided by the blade mounting system. The histology radius trimming blade embodies a radiused or otherwise uniquely shaped heel for cutting and dissecting tissue specimens taken from patients in medical laboratories for anatomical pathology applications, including but not limited to grossing, sectioning, post-mortem examination, and medical research.

Referring now to FIGS. 1 through 9, the present invention may include a histology radius blade grossing knife 100. The histology radius blade grossing knife 100 may include various types of uniquely shaped heeled trimming knife blades 10, 74, and 78, a handle 30, a blade retainer spine 20, and a blade mounting system 90 adapted to retain one of the trimming knife blades 10, 74, and 78 to the handle 30 for use in the above-mentioned anatomical pathology applications.

The trimming knife blades 10, 74, and 78 may have a rounded radius blade heel 12, a straight edge blade heel 76, or a segmented angled blade heel 80, respectively, so as to be adapted for smoother cutting and dissecting of tissue specimens taken from patients in medical laboratories. The rounded radius blade heel 12 may be defined by a curvature having a radius of approximately 1.00 inch, ranging between 0.95 and 1.05 inch in radius. The curvature may be further defined by a rise of between 0.15 and 0.17 inches and a run between 0.45 and 0.55 inches. The straight edge blade heel 76 may be defined by a straight edge interconnecting said rise and said run. The segmented angled blade heel 80 may have a first segmented edge 81 and a second segmented edge 82 oblique relative to the first segmented edge, and wherein the second segmented edge 82 is longer than the first segmented edge 81. Each blade 10, 74, and 78 may provide a hanging hole 14.

The handle 30 and spine 20 are interconnected by a blade mounting system 90. The handle 30 may be any material with the durability and strength to be used as described herein, such as molded plastic material. The blade mounting system 90 may provide a first retainer plate 41 connected to a distal end of the handle 30.

Figure 3:
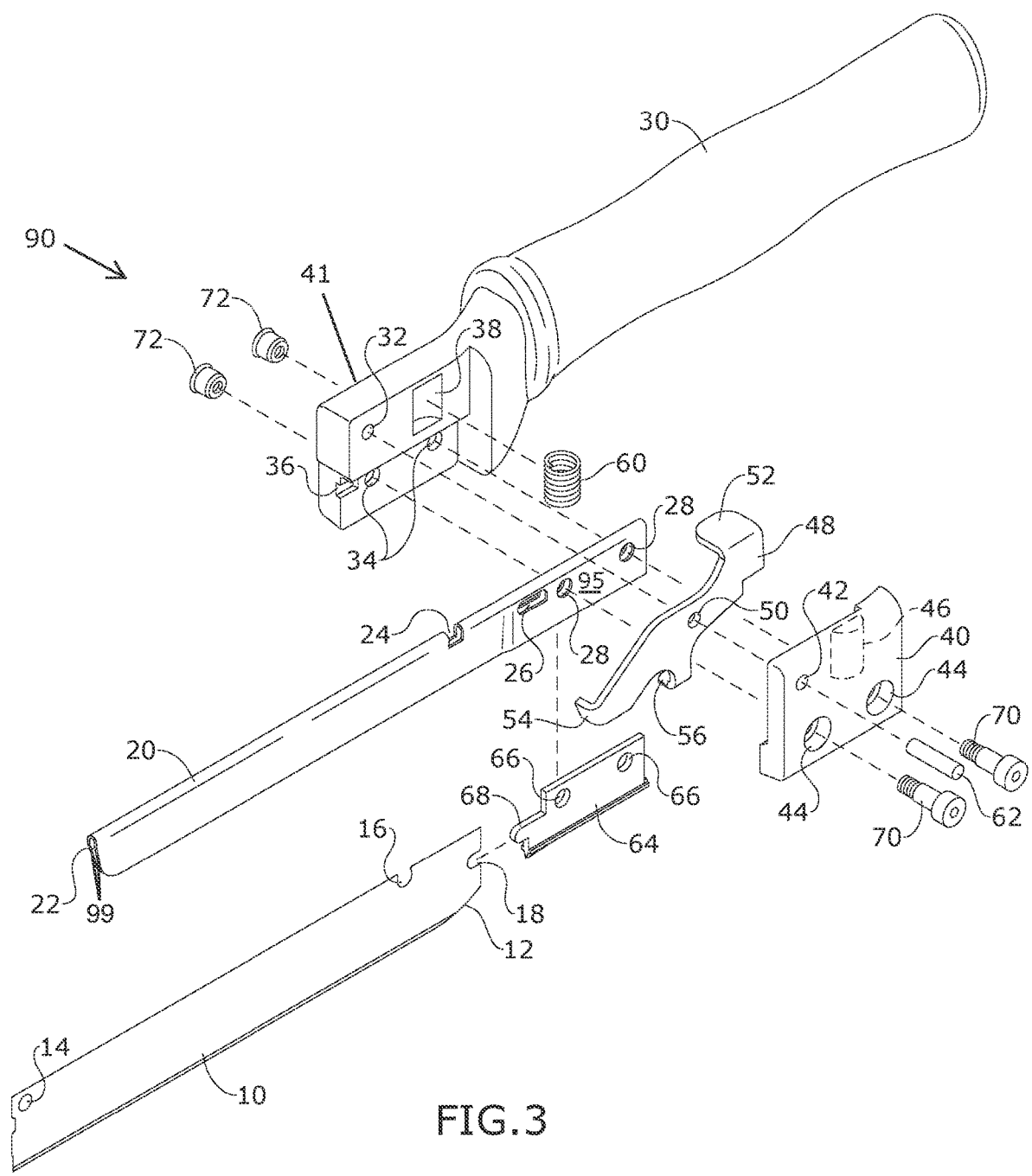
FIG. 3 is an exploded view of an exemplary embodiment of the present invention.
Figure 6:
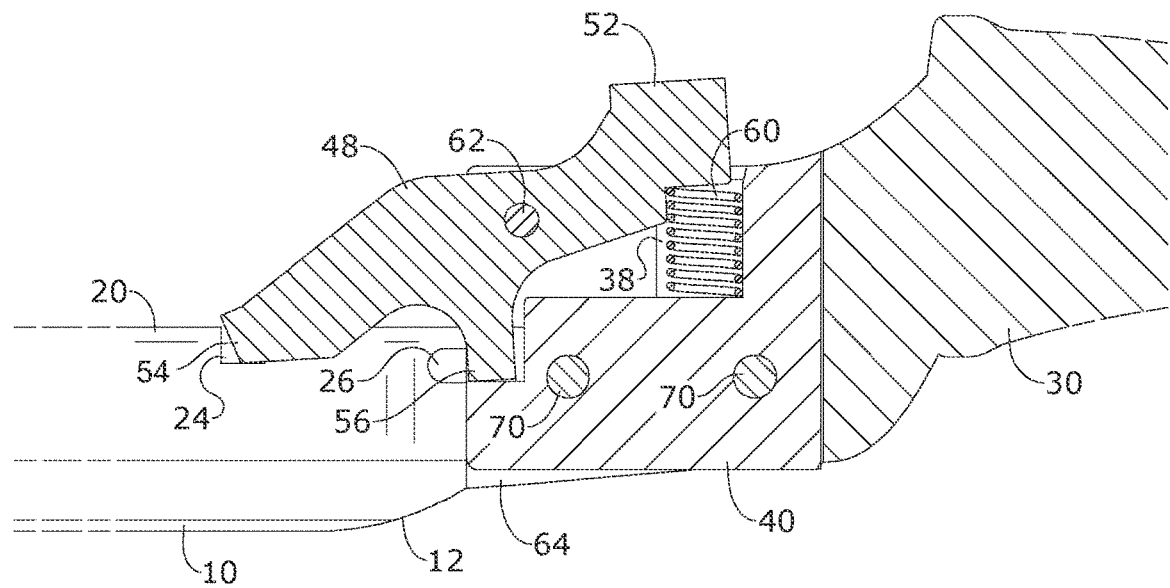
FIG. 6 is a section view of an exemplary embodiment of the present invention, taken along line 6-6 in FIG. 4.
Figure 7:
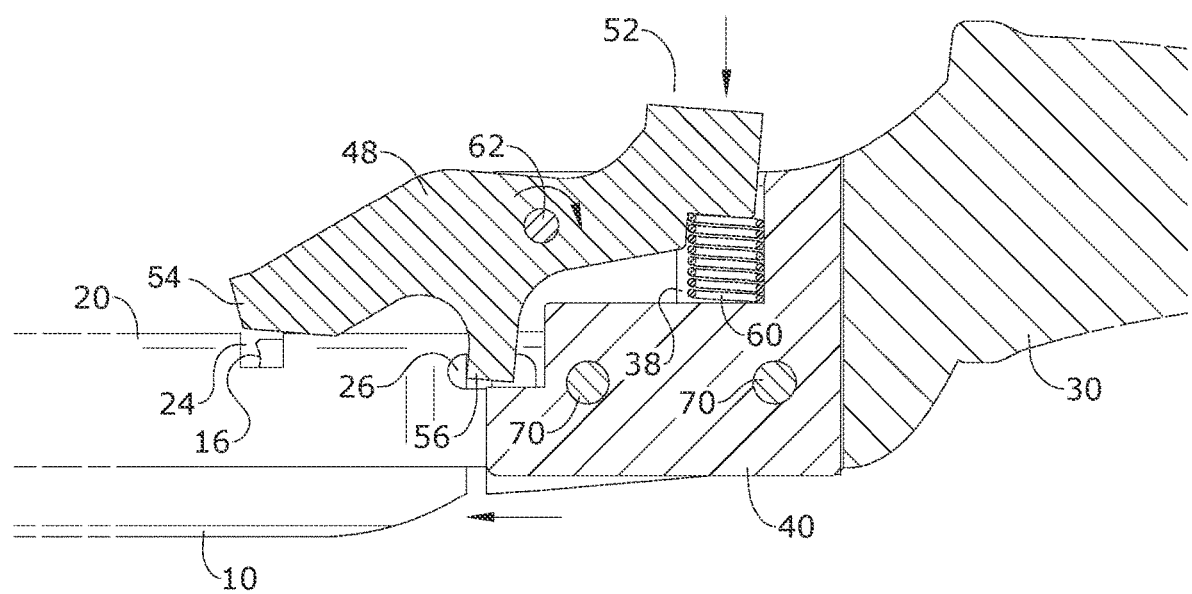
FIG. 7 is a section view of an exemplary embodiment of the present invention, illustrating the depression of latch 48 to release blade 10.
Figure 8:
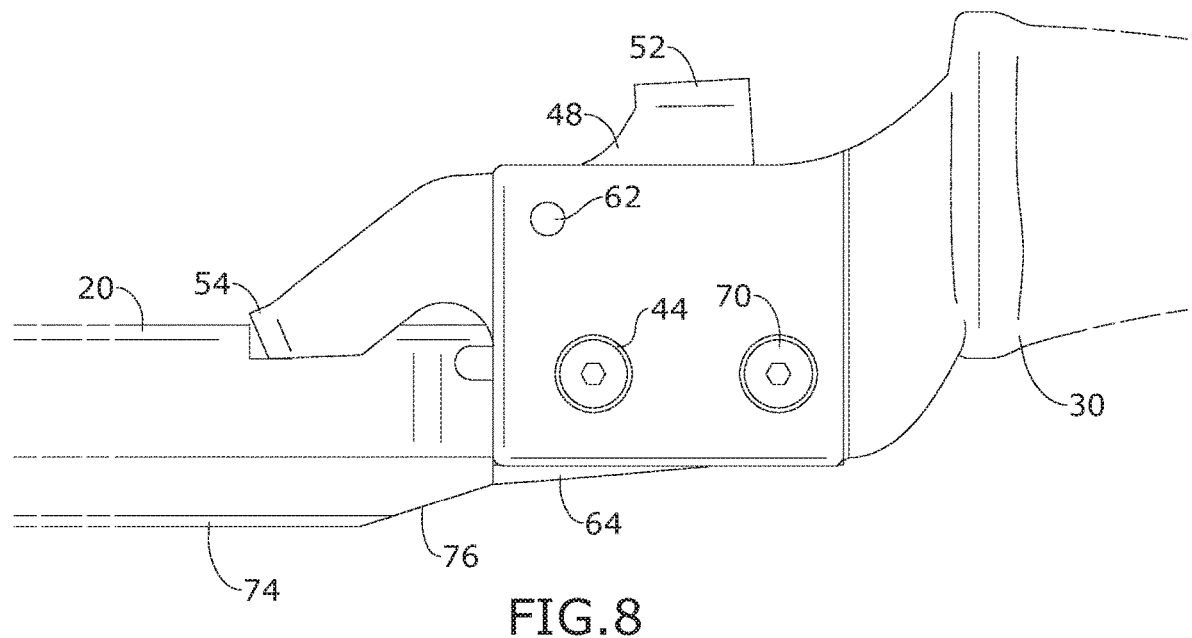
FIG. 8 is a side view of an exemplary embodiment of the present invention.
Figure 9:
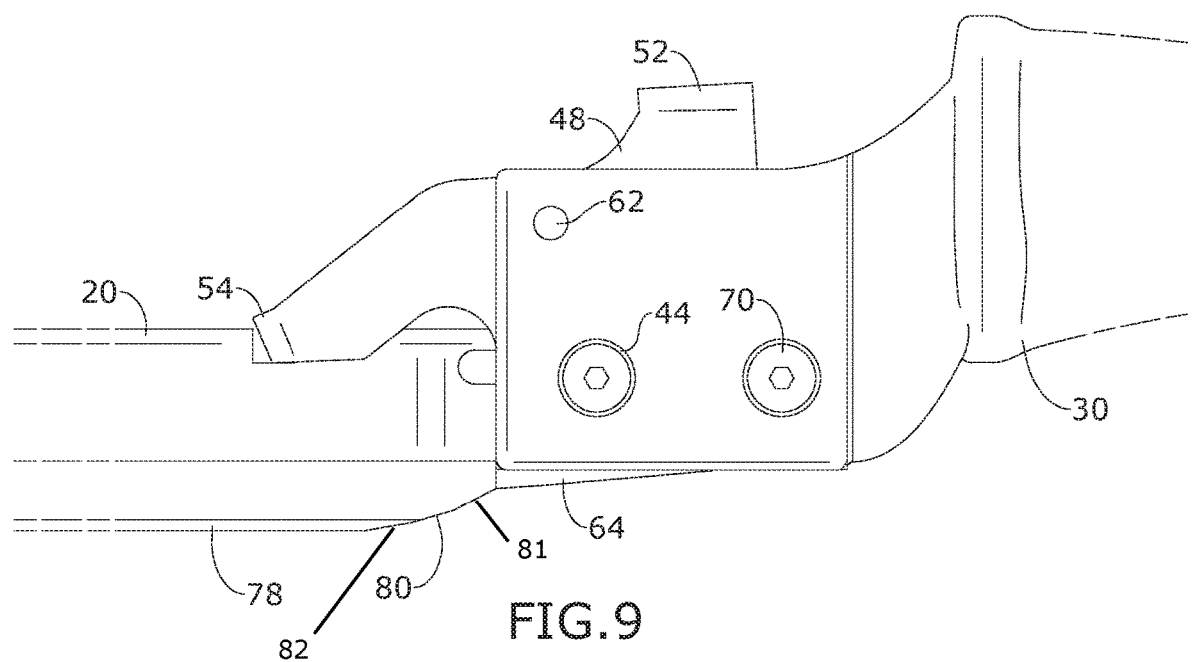
FIG. 9 is a side view of an exemplary embodiment of the present invention.

In certain embodiments, the spine 20 may have a small narrow slot 22 that allows an upper edge the blade (10, 74, or 78) to be slidably received and engaged by tension. The spine 20 may have a folded shape, wherein the lower lengthwise edges 99 taper towards each other for engaging the upper edge of the relevant blade, as illustrated in FIG. 3. Along the opposing upper rounded lengthwise edge is a spine locking tab notch 24. A proximal portion 95 of the spine 20 may provide a release tab slot 26 along a side portion thereof, as illustrated in FIG. 3. The upper edge of each blade 10, 74, or 78 provides a corresponding knife locking tab notch 16 that aligns with the spine locking tab notch 24 when the associated blade 10, 74, or 78 is received in the spine 20.

The present invention may include a separate pivotable connected thumb latch 48 pivotable between a locked position and an open position. The latch 48 may provide a thumb tab 52 for facilitating such pivoting. The latch 48 may provide a locking tab 54 that is received in the spine locking tab notch 24 (and thus the knife locking tab notch 16 of a blade properly received by the spine 20) in a locking engagement. The latch 48 may provide a blade release tab 56 that also moves along with the locking tab 54, wherein the blade release tab 56 slides along the release tab slot 26 of the spine 20 and an associated systemic release tab slot 36 provide by the first retainer plate 41. The pivotable latch 48 pivots about a pivot pin 62 disposed through a pivot hole 50 in the body of the latch 48.

Referring to FIG. 3, the first retainer plate 41 also provides a corresponding pivot hole 32, insert holes 34, as well as a spring slot 38 housing a spring 60 that operatively associates with the body of the latch 48 for pivoting between the locked position and the open position. By way of fasteners 70 and 72 (passing through the spine's 20 insert holes 28) the first retainer plate 41 s securely sandwiches the proximal portion 95 of the spine 20 against a second retainer plate 40 providing slot holes 44 for engaging said fasteners 70 and 72. The second retainer plate 40 also provides a pivot hole 42 for receiving the pivot pin 62 and a complementary spring slot 46 as well.

A blade stop 64 (having fastener insert holes 66 also adapted for associating with fasteners 70 and 72) may nest within the proximal portion 95 of the blade spine 20. Along said proximal portion 95, the lower lengthwise edges may not be tapered towards each other (like the remaining portion of the blade spine 20) so as to accommodate the nested blade stop 64. The blade stop 64 provides a protruding stop tab 68 that operatively engages a stop notch 18 along a rear edge of the relevant blade 10, 74 and 78.

Each blade 10, 74 or 78 has two notches (the stop notch 18 and the locking tab notch 16) for securement. The rear stop notch 18 mates with the protruding stop tab 68 provided by the blade stop 64 housed in the blade spine 20. As mentioned above, the handle 30 provides the pivotable thumb latch 48 with locking tab 54 that seats down into the top locking tab notch 16. These two notches 16 and 18 work together to secure the blade safely in the blade retainer spine 20, eliminating the need for securing screws found in the prior art. The thumb latch 48 also has a second lever on it that pushes the blade to aid in blade removal.

It should be understood, of course, that the foregoing relates to exemplary embodiments of the invention and that modifications may be made without departing from the spirit and scope of the present invention as set forth in the following claims.

What is claimed is:

1. An apparatus for removably engaging a histology trimming blade, the histology trimming blade having a first portion, the first portion comprising a blade locking notch, the apparatus comprising:
 a handle having a first retaining plate;
 a spine having a spine locking notch;
 the spine configured for engaging the first portion for alignment of the spine locking notch and the blade locking notch;
 a thumb latch having a locking tab and a release tab; and
 the thumb latch pivotably connected to the first retaining plate in such a way that the locking tab pivots between an open position and a locked position, wherein the locking tab engages the spine locking notch in the locked position, wherein the release tab is configured to engage the histology trimming blade as the thumb latch moves the locking tab from the locked position toward the open position, and wherein in the open position the locking tab is moved away from the spine.

2. The apparatus of claim 1, wherein the spine has two lengthwise edges tapering toward each other.

3. The apparatus of claim 2, wherein the histology trimming blade further has a stop notch in a rear portion thereof;

further comprising a blade stop nested between the two lengthwise edges; and the blade stop comprises a protruding stop tab for mating with the stop notch.

4. The apparatus of claim 3, wherein the spine further has a tab slot proximal the spine locking notch, and wherein the release tab is configured to urge the histology trimming blade as the thumb latch moves the locking tab from the locked position toward the open position.

5. The apparatus of claim 4, wherein the release tab is configured to urge the histology trimming blade away from the first retaining plate as the thumb latch moves the locking tab from the locked position to the open position.

\* \* \* \* \*